United States Patent [19]

Harris et al.

[11] Patent Number: 4,587,238

[45] Date of Patent: May 6, 1986

[54] SUBSTITUTED CAPRYLOLACTAM DERIVATIVES AS ANTI-HYPERTENSIVES

[75] Inventors: Elbert E. Harris; Arthur A. Patchett, both of Westfield; Eugene D. Thorsett, Fanwood, all of N.J.

[73] Assignee: Merck & Co., Inc., Rahway, N.J.

[21] Appl. No.: 396,583

[22] Filed: Jul. 9, 1982

Related U.S. Application Data

[63] Continuation-in-part of Ser. No. 280,667, Jul. 6, 1981, abandoned, which is a continuation-in-part of Ser. No. 179,321, Aug. 18, 1980, abandoned.

[51] Int. Cl.$^4$ .................... A61K 31/33; C07D 225/02
[52] U.S. Cl. .................... 514/183; 260/239.3 R; 514/340; 514/314; 514/443; 514/444; 514/438; 514/471; 514/397; 514/372; 514/365; 514/415; 514/417
[58] Field of Search ................. 260/239.3 R; 424/244, 424/273 R, 274

[56] References Cited

U.S. PATENT DOCUMENTS 4,052,511 10/1977 Cushman et al. ............... 260/239 A
4,129,571 12/1978 Ondetti et al. ..................... 546/208
4,154,960  5/1979 Ondetti et al. ..................... 546/208

*Primary Examiner*—Robert T. Bond
*Attorney, Agent, or Firm*—Salvatore C. Mitri; Michael C. Sudol

[57] ABSTRACT

The invention in its broad aspects relates to caprylolactam derivatives which are useful as angiotensin converting enzyme inhibitors and as antihypertensives.

9 Claims, No Drawings

SUBSTITUTED CAPRYLOLACTAM DERIVATIVES AS ANTI-HYPERTENSIVES

This is a continuation-in-part application of pending application Ser. No. 280,667 filed July 6, 1981, now abandoned, which, in turn, is a continuation-in-part application of application Ser. No. 179,321 filed Aug. 18, 1980, now abandoned.

BACKGROUND OF THE DISCLOSURE

The invention in its broad aspects relates to caprylolactam derivatives which are useful as angiotensin converting enzymme inhibitors and as antihypertensives. The compounds of this invention can be shown by the following formula:

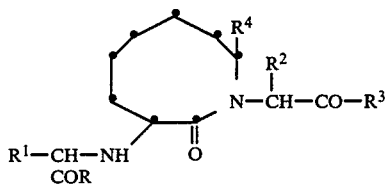

wherein
R and $R^3$ are the same or different and are
  hydroxy,
  lower alkoxy,
  lower alkenoxy,
  aryloxy such as phenoxy,
  arloweralkoxy, such as benzyloxy;
$R^1$ is
  hydrogen,
  alkyl of from 1 to 12 carbon atoms which include branched and cyclic and unsaturated (such as allyl) alkyl groups,
  substituted loweralkyl wherein the substituent(s) can be halo, lower alkoxy, hydroxy, aryloxy (such as phenoxy), amino, lower alkylamino, aminoloweralkylthio, aminolower alkoxy, diloweralkylamino, acylamino, (such as acetamido and benzamido), arylamino, (such as phenylamino), guanidino, phthalimido, mercapto, loweralkylthio, arylthio (such as phenylthio), carboxy, carboxamido or carboloweralkoxy,
  arloweralkyl, arloweralkenyl, heteroarlower alkyl or heteroarlower alkenyl (such as benzyl, styryl, indolylethyl, imidazolylmethyl, naphthylethyl),
  substituted arloweralkyl, or substituted heteroarlower alkyl, wherein the aryl or heteroaryl substituents are halo, dihalo, lower alkyl, hydroxy, lower alkoxy, amino, aminomethyl, phenyloxy, acylamino, diloweralkylamino, loweralkylamino, carboxyl, haloloweralkvl, acyl or aroyl;
  arloweralkyl or heteroarloweralkyl substituted on the alkyl portion bv amino, hydroxyl or acylamino;
$R^2$ and $R^4$ are hydrogen or lower alkyl; and, the pharmaceutically acceptable salts thereof.

As used throughout this application, including the claims, and unless specified otherwise:
alkyl denotes straight and branched hydrocarbons of $C_1$–$C_{12}$ and loweralkyl denotes straight and branched hydrocarbons of $C_1$–$C_8$;
alkenyl denotes straight and branched hydrocarbons of $C_2$–$C_{12}$ and loweralkenyl denotes straight and branched hydrocarbons of $C_2$–$C_8$, each of which contain a double bond;
alkynyl denotes straight and branched hydrocarbons of $C_2$–$C_{12}$ and loweralkynyl denotes straight and branched hydrocarbons of $C_2$–$C_8$, each of which contain a triple bond;
aryl and the prefix "ar" denote unsubstituted aromatic ring or rings of C—C such as, for example, phenyl, naphthyl, biphenyl;
acyl denotes a carboxylic acid derivative represented by the formula

wherein R is alkane, aralkane, arene, heteroarene, heteroaralkene, and substituted derivatives thereof so that acyl denotes, for example, alkanoyl, aroyl, aralkanoyl, heteroaryl, heteroaralkanoyl, and the like;
cycloalkyl denotes an unsubstituted alkyl ring of $C_3$–$C_{10}$;
hetero denotes the heteroatoms N, O
heteroaryl denotes an aryl group containing a heteroatom;
heterocycle denotes a saturated or unsaturated aromatic or non-aromatic cyclic compound containing a heteroatom;
halogen and halo denote F, Br, Cl or I atoms; and,
alkoxy denotes a $C_1$–$C_6$ alkyl with O.

Exemplary loweralkyl or lower alkenyl groups include, for example, methyl, ethyl, propyl, isopropyl, butyl, isobutyl, t-butyl, pentyl, isopentyl, hexyl or vinyl, allyl, butenyl and the like, and exemplary aralkyl groups include, for example, benzyl, p-methoxybenzyl and the like. Illustrative heteroaryl groups include, for example, pyridyl, thienyl, furyl, indolyl, benzthienyl, imidazoyl thiazolyl and quinolinyl.

Preferred are those compounds of Formula I wherein:
R and $R^3$ are independently hydroxy, lower alkoxy, or benzyloxy;
$R^1$ is alkyl having from 1 to 8 carbon atoms, substituted lower alkyl wherein the alkyl group has 1–5 carbon atoms and the substituent is amino, acylamino, hydroxy, aminoloweralkylthio, aminoloweralkoxy, arylthio, aryloxy or arylamino, aralkyl or heteroaralkyl wherein the alkyl portion has 1 to 3 carbon atoms (such as phenethyl or indolylethyl) or substituted arloweralkyl (phenyl lower alkyl or naphthyl lower alkyl) and substituted heteroarloweralkyl wherein the alkyl groups have 1–3 carbons optionally substituted with amino, hydroxy, or acylamino and wherein the substituents on the aryl or heteroaryl group are halo, dihalo, amino, aminoalkyl, hydroxy, lower alkoxy, lower alkyl, phenoxy or benzoyl;
$R^2$ and $R^4$ are hydrogen or lower alkyl.

More preferred are compounds of Formula I wherein
$R^2$ is hydrogen or lower alkyl;
$R^4$ is hydrogen;
$R^1$ is alkyl from 1 to 8 carbon atoms, phenyl lower alkyl, indolyl lower alkyl, halo phenyl lower alkyl, phenoxy lower alkyl, amino lower alkyl, phenyl thio lower alkyl, aminoethylthio lower alkyl, aminoethyloxy lower alkyl;
R and $R^3$ are independently hydroxy, lower alkoxy, benzyloxy.

Most preferred are compounds of Formula I wherein $R^2$ and $R^4$ are hydrogen;

$R^1$ is phenyl lower alkyl, indolyl lower alkyl, halophenyl lower alkyl, amino lower alkyl;

R and $R^3$ are independently hydroxy, lower alkoxy or benzyloxy.

The preferred, more preferred and most preferred compounds also include the pharmaceutically acceptable salts thereof.

The products of Formula (I) and the preferred subgroups can be produced by one or more of the methods and subroutes depicted in the following equations. The definitions of R, $R^1$, $R^2$, $R^3$, and $R^4$ are the same as in Formula (I) except where noted.

METHOD A

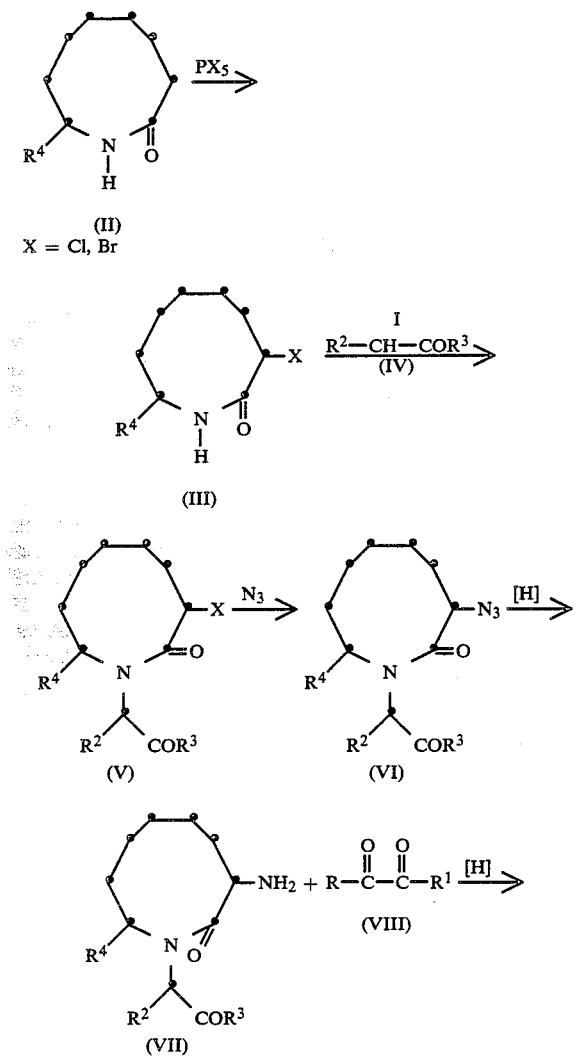

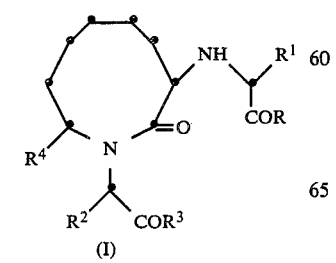

METHOD B

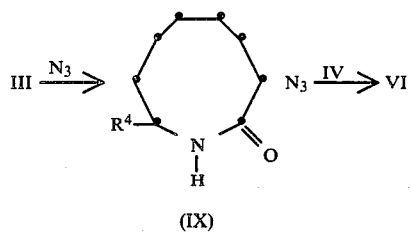

The perhydroazonin-2-one (II), prepared from cycloactenone by the procedure of Blicke et al., [J. Am. Chem. Soc., 76, 2317 (1954)] or from a substituted cyclooctenone as described by Wilson, et. al., J. Org. Chem., 44, 330 (1979) followed by catalytic hydrogenation, is converted to (III) with $PX_5$ (X=CL or Br) [Nagasawa et al., J. Med. Chem., 14, 501 (1971)]. Reaction of (III) with an iodoester (IV) in the presence of a strong base, such as sodium hydride, in a suitable solvent like DMF or THF affords (V). Treatment of (V) with an azide salt, such as lithium azide, in a solvent, like DMF, gives (VI) which upon reduction with hydrogen and a catalyst such as palladium produces amine (VII). Reductive amination of an α-keto ester or acid (VIII) with amine (VII) using sodium cyanoborohydride or hydrogen and a suitable catalyst such as palladium or Raney nickel in a suitable solvent, such as ethanol, affords (I).

Groups R and $R^3$ can be modified by known methods, if desired. For example, if R=OEt and $R^3$=O—t—Bu, the diester (I) can be converted to the monoester, $R^3$=OH, by treatment with trifluoroacetic acid. If R=$R^3$=OEt or $R^3$=OH and R=OEt, for example, (I) can be converted to the diacid R=$R^3$=OH by basic hydrolysis. Alternatively (III) can be converted to azide (IX) as described above. Reaction of (IX) with (IV) as described above affords (VI) which can be converted to (I) by the described methods.

The starting materials which are required for the above processes herein described are known in the literature or can be made by known methods from known starting materials.

In products of general Formula (I), the carbon atom to which, $R^1$, $R^2$ and $R^4$ are attached and the ring carbon atom to which the fragment

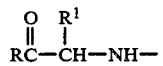

is attached are asymmetric ($R^1$, $R^2$ and $R^4 \neq H$). The compounds accordingly exist in diastereoisomeric forms or as enantiomers, or in mixtures thereof. The above described syntheses can proceed through racemates, enantiomers or diastereomers. When diastereomeric products result from the synthetic procedures, the diastereomeric products can be separated by chromatographic or fractional crystallization methods. When racemic products result, they may be resolved by crystallization of salts of optically active acids or bases or by other methods known in the art. The part-structures,

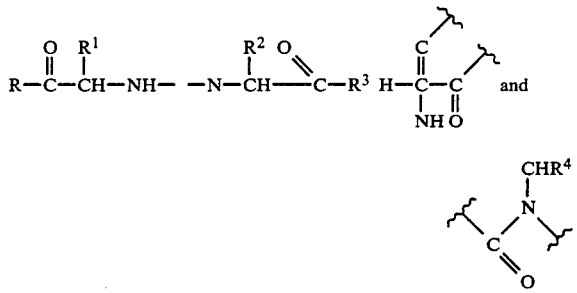

of Formula (I) can be in two configurations (S or R) and both are within the scope of this invention although S is generally preferred except at the carbon atom to which $R^4$ is attached.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases, e.g., dicyclohexylamine salts, N-methyl-D-glucamine, salts with amino acids like arginine, lysine and the like. Also salts with organic and inorganic acids may be prepared; e.g., HCl, HBr, $H_2SO_4$, $H_3PO_4$, methanesulfonic, toluenesulfonic, maleic, fumaric, camphorsulfonic acids. The non-toxic physiologically acceptable salts are particularly valuable, although other salts are also useful, e.g., in isolating or purifying the product.

The salts may be formed by conventional means, as by reacting the free acid or free base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The compounds of this invention inhibit angiotensin converting enzyme and thus block conversion of the decapeptide angiotensin I to angiotensin II. Angiotensin II is a potent pressor substance. Thus blood-pressure lowering results from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta*, 206, 136 (1970) in which the hydrolysis of carbobenzyloxyphenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.*, 104, 646 (1960) or in a high renin rat model such as that of S. Koletsky et al., *Proc. Soc. Exp. Biol. Med.*, 125, 96 (1967).

Thus, the compounds of this invention are useful as antihypertensives in treating hypertensive mammals, incuding humans and they can be utilized to achieve the reduction of blood pressure by formulating in compositions such as tablets, capsules or elixirs for oral administration or in sterile solutions or suspensions for parenteral administration. The compounds of this invention can be administered to patients in need of such treatment in a dosage range of 1.0 to 100 mg oer patient optionally given several times, thus giving a total daily dose of from 1.0 to 400 mg per day. The dose will vary depending on severity of disease, weight of patient and other factors which a person skilled in the art will recognize.

Also, the compounds of this invention may be given in combination with diuretics or other antihypertensives. Typically these are combinations whose individual per day dosages range from one-fifth of the minimally recommended clinical dosages to the maximum recommended levels for the entities when they are given singly. To illustrate these combinations, one of the antihypertensives of this invention effective clinically in the range 2.5-100 milligrams per day can be effectively combined at levels ranginq from 0.5-100 milligrams per day with the following antihypertensives and diuretics in dose ranges per day as indicated: hydrochlorothiazide (10-200 mg), timolol (5-60 mg), methyl dopa (65-2000 mg), the pivaloyloxyethyl ester of methyl dopa (30-1000 mg), indacrinone and variable ratios of its enantiomers (25-150 mg) and (+)-4-{3{-[2-(1-hydroxycyclohexyl)-ethyl]-4-oxo-2-thiazolidiny}propyl}-benzoic acid (10-100 mg).

In addition, the triple drug combinations of hydrochlorothiazide (15-200 mg) plus amiloride (5-20 mg) plus converting enzyme inhibitor of this invention (3-200 mg) or hydrochlorothiazide (15-200 mg) plus timolol (5-50 mg) plus the converting enzyme inhibitor of this invention (3-200 mg) are effective combinations to control blood pressure in hypertensive patients.

The above dose ranges will be adjusted on a unit basis as necessary to permit divided daily dosage. Also, the dose will vary depending on the severity of the disease, weight of patient and other factors which a person skilled in the art will recognize.

Typically the compounds and combinations shown above are formulated into pharmaceutical compositions as discussed below.

About 1.0 to 100 mg of a compound or of Formula I or a physiologically acceptable salt thereof or a mixture with diuretic and/or other antihypertensive compounds is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The following examples are illustrative of the invention and constitute especially preferred embodiments. The preferred diastereomers of these examples are isolated by column chromatography or fractional crystallization. Optical isomers are separated through the use of optically active acids or bases as resolving agents.

EXAMPLE 1

1-Carboxymethyl-3-[(1-carboxy-3-phenylpropyl)amino]-perhydroazonin-2-one and monoethyl ester Add a solution of 7.35 g. 3-bromoperhydroazonin-2-one [Nagasawa et al., J. Med. Chem., 14, 501 (1971)] and 8.47 g t-butyl iodoacetate in 70 ml THF to a suspension of 0.881 g sodium hydride in 35 ml THF. After 2 hours at room temperature, add 15 ml saturated $NH_4Cl$ solution, filter and concentrate the filtrate in vacuo. Partition the residue between ether and $H_2O$ and wash the organic phase with $H_2O$ and brine. Dry the ether solution and filter. Decolorize the filtrate with charcoal, filter and concentrate the filtrate in vacuo to isolate 3-bromo-1-t-butoxycarbonylmethylperhydroazonin-2-one. Purify a sample for characterization by silica gel chromatography. Anal. $C_{14}H_{24}BrNO_3$). Calc: C, 50.31; H, 7.24; N, 4.18; Br, 23.91. Found: C, 49.86; H, 7.33; N, 4.30; Br, 23.51. Mass spectrum: $M^+$ at 334; m/e: 278 ($M^+-C_4H_8$), 261 ($M^+-C_4H_9O$); 232 ($M^+-C_4H_9CO_2-H$, base).

Dissolve 2.81 g lithium azide in 60 ml DMF and add 6.5 g of bromolactam ester to the solution. Heat the solution at 80° for 20 hr. Concentrate the reaction in vacuo and partition the residue between $H_2O$ and $CH_2Cl_2$. Wash the organic phase with $H_2O$, dry, filter and concentrate the filtrate to isolate 3-azido-1-t-butoxycarbonylmethylperhydro- azonin-2-one. IR: $N_3$, 2150 $cm^{-1}$; CO, 1680, 1765 $cm^{-1}$.

Dissolve 4.74 g of this azide in 75 ml ethanol and add 475 mg 10% palladium on charcoal. Hydrogenate the mixture under 40 psig hydrogen pressure. Filter and concentrate the filtrate in vacuo to isolate 3-amino-1-t-butoxycarbonylmethylperhydroazonin-2-one.

Combine 2.0 g of this aminolactam, 2.29 g ethyl 2-oxo-4-phenylbutyrate, 0.41 ml acetic acid and 375 mg 10% palladium on charcoal in 60 ml ethanol. Hydrogenate this mixture under 40 psig hydrogen. Filter the reaction and concentrate the filtrate in vacuo. Chromatograph the residue on silica gel using 3:2 hexane:ethyl acetate and isolate two diastereomeric racemates of 1-t-butoxycarbonylmethyl-3-[(1-ethoxy-carbonyl-3-phenylpropyl)amino]perhydro- azonin-2-one.

Isomer A elutes first from the column.

Mass spectrum: $M^+$ at 460; m/e: 403 ($M^+-C_4H_9$), 387 ($M^+-C_2H_5CO_2$). NMR ($CCl_4$, TMS): $\delta1.25$ (t, 3H), $\delta1.4-2.05$ (m, 21H); $\delta2.5-3.8$ (m, 7H); $\delta3.8-4.3$ (s+q, 4H); $\delta7.15$ (s, 5H).

Isomer B elutes second from the column.

Mass spectrum: $M^+$ at 460; m/e: 403 ($M^+-C_4H_9$), 387 ($M^+-C_2H_5CO_2$).

Dissolve 460 mg isomer B in 2 ml trifluoroacetic acid and store at room temperature for 1.5 hours. Concentrate the solution to obtain 1-carboxymethyl-3-[(1-ethoxycarbonyl-3-phenylpropyl)amino]perhydroazonin-2-one trifluoroacetate.

Anal. ($C_{22}H_{32}N_2O_5 \cdot CF_3CO_2H$): Calc: C, 55,59; H, 6.41; N, 5.40. Found: C, 55,35; H, 6.47; N, 5.31.

Mass spectrum: $M^+$ at 404 ($-CF_3CO_2H$).

m/e: 331 ($M^+-C_2H_5$, base).

Dissolve 300 mg of this monoester salt (Isomer B) in 4 ml 1N NaOH and store the solution at room temperature for 20 hours. Pass the solution through a Dowex 50 ($H^+$) column eluting first with $H_2O$, then 5% pyridine. Isolate the isomer B diacid. Mass spectrum $M^+$ at 376. m/e; 358 ($M^+-H_2O$): 331 ($M^+-CO_2H$).

Repeat the above process on the Isomer A diester to obtain the Isomer A diacid.

Mass spectrum (bis-trimethylsilyl derivative): $M^+$ at 521 ($M+1H$).

m/e: 506 ($M^+-CH_3$), 404 ($M-(CH_3)_3SiCO_2$).

EXAMPLE 2

1-(1-Carboxyethyl)-3-[(1-ethoxycarbonyl-3-phenylpropyl) -amino]perhydroazonin-2-one Prepare a solution of 250 mq lithium azide in 6 ml of DMF and add to it 426 mg 3-bromoperhydroazonin-2-one. Heat the reaction at 70° under nitrogen for 24 hours. Concentrate the reaction in vacuo, dissolve the residue in $H_2O$ and extract with ethyl acetate. Dry and concentrate the extracts and chromatograph the residue on silica gel with ethyl acetate-acetonitrile. Isolate 3-azidoperhydroazonin-2-one.

Add 170 mg of this azide to a suspension of 30 mg NaH in 3 ml THF followed by a solution of 400 mg methyl 2-iodoproprionate in 2 ml THF. Heat the reaction mixture under nitrogen at 55° for 18 hr. Cool the reaction and add a few drops of $H_2O$ followed by ether. Wash the mixture with 5% $NaHSO_3$, water, and brine. Dry the organic phase and concentrate in vacuo. Chromatograph this crude product on silica gel eluting with ethyl acetatehexane and isolate 3-azido-1-(1-carbomethoxyethyl)- perhydroazonin-2-one. Hydrolyze this ester in 1M NaOH. Acidify the reaction and extract with methylene chloride to obtain 3-azido-1-(1-carboxyethyl)perhydroazonin-2-one. Separate the diastereomers by reverse phase chromatography using acetonitrile-water mixtures.

Dissolve the first diastereomer which elutes (Isomer A) in aqueous ethanol and hydrogenate using palladium on carbon catalyst to obtain 3-amino-1-(1-carboxyethyl)perhydroazonin-2-one.

Dissolve 226 mg of this amino acid in absolute ethanol and add 1.03 g ethyl 2-oxo-4-phenylbutyrate. Hydrogenate this solution using 10% palladium on carbon as catalyst. Filter and concentrate the reaction. Purify the crude reaction product on Dowex 50 ($H^+$). Isolate, after elution with aqueous pyridine, 1-(1-carboxyethyl)-3-[(1-ethoxycarbonyl-3-phenylpropyl)amino]perhydroazonin-2-one as a mixture of isomers.

In the same manner, hydrogenate the second diasteroisomer which elutes from the reverse phase chromatography (Isomer B) and couple with ethyl 2-oxo-4- phenylbutyrate to obtain, after purification, the additional set of isomers of 1-(1-carboxyethyl)-3-[(1-ethoxycarbonyl-3-phenylpropyl)amino]perhydroazepin-2-one.

EXAMPLE 3

1-Carboxyethyl-3-[(1-benzyloxycarbonyl-3-phenylpropyl)amino]perhydroazonin-2-one Dissolve 228 mg 3-amino-1-carboxyethylperhydroazonin-2-one (Isomer A) in $H_2O$, adjust the pH to 6 with NaOH and freeze-dry the solution. Dissolve the solid in 10 ml ethanol, add 1.34 g benzyl 2-oxo-4-phenyl-butyrate and 250 mg sodium cyanoborohydride, and stir the mixture at room temperature for 24 hours. Quench the reaction with HCl. Concentrate the mixture in vacuo, and chromatograph the residue on Dowex 50 (H+). Isolate, after pyridine elution, the desired monoesters as a mixture of diastereomers. Separate the diastereomers chromatographically. Repeat the process on the Isomer B amine to obtain the other set of isomeric esters.

EXAMPLE 4

1-(1-Ethoxycarbonylethyl)-3-[(1-ethoxycarbonyl-3-phenylpropyl)amino]perhydroazonin-2-one Hydrogenate 2.42 g 1-(1-ethoxycarbonylethyl)-3-aminoperhydroazonin-2-one and 3.09 g ethyl 2-oxo-4-phenylbutyrate in 100 ml ethanol containing 0.60 g acetic acid as described in Example 1.

Separate the diastereomeric esters by silica gel chromatography using hexane-ethyl acetate mixtures.

EXAMPLE 5

1-(1-Carboxyethyl)-3-[(1-carboxy-3-phenylpropyl)amino]perhydroazonin-2-one

The diastereomerically pure benzyl ester products of Example 3 are separately treated with excess 1N NaOH in 50% ethanol at room temperature for 18 hours. Work-up according to Example 1 affords, after lyophilization, the title diastereomerically pure diacids. These same diacid products can also be prepared by saponification of the diethyl ester products of Example 4.

EXAMPLE 6

Monoester Products

3-Amino-1-t-butoxycarbonylmethylperhydroazonin-2-one is reductively condensed with the α-ketoesters listed in Table I below in place of ethyl 2-oxo-4-phenylbutyrate using the palladium on charcoal method described in Example 1. Work-up, including t-butoxy removal, as described in Example 1 affords the corresponding products listed in Table II below.

Alternatively, sodium cyanoborohydride may be used in the reductive condensation. In this procedure, a solution of 100 mg 3-amino-1-t-butoxy- carbonylmethylperhydroazonin-2-one and 3-5 equivalents of an ester listed in Table I is prepared in 6 ml ethanol containing 1 equivalent of acetic acid. A solution of 1.5-3 equivalents of sodium cyanoborohydride in 1.5 ml ethanol is added over a period of 6-24 hours. The reaction mixture is filtered, and the concentrated filtrate is partitioned between $H_2O$ and $CH_2Cl_2$. The organic portion is dried, concentrated and chromatographed to yield product as described in Example 1.

TABLE I

| | | α-Ketoesters |
|---|---|---|
| a | Benzyl | 2-oxo-4-phenylbutyrate |
| b | Ethyl | 4-p-chlorophenyl-2-oxobutyrate |
| c | Ethyl | 4-(3-indolyl)2-oxobutyrate |
| d | Ethyl | 2-oxo-4-(2-thienyl)butyrate |
| e | Ethyl | 2-oxo-4-(2-naphthyl)butyrate |
| f | Ethyl | 4-p-hydroxyphenyl-2-oxobutyrate |
| g | Ethyl | phenoxypyruvate |
| h | Ethyl | 2-oxo-5-phenylpentanoate |
| i | Ethyl | 4-p-methoxyphenyl-2-oxobutyrate |
| j | Ethyl | 5-methyl-2-oxohexanoate |
| k | Benzyl | 2-oxo-6-phthalimidohexanoate |

TABLE II

| | Products of Formula I ($R^2 = R^4 = H$; $R^3 = OH$) | |
|---|---|---|
| | R | $R^1$ |
| l | Benzyloxy | phenethyl |
| m | Ethoxy | p-chlorophenethyl |
| n | Ethoxy | 3-indolylethyl |
| o | Ethoxy | 2-thienylethyl |
| p | Ethoxy | 2-naphthylethyl |
| q | Ethoxy | p-hydroxyphenethyl |
| r | Ethoxy | phenoxymethyl |
| s | Ethoxy | 3-phenylpropyl |
| t | Ethoxy | p-methoxyphenethyl |
| u | Ethoxy | 3-methylbutyl |
| v | Benzyloxy | 4-phthalimidobutyl |
| *w | Benzyloxy | 4-aminobutyl |

*After hydrazinolysis of (v) under standard conditions.

EXAMPLE 7

Diacid Products

Saponification of the esters using the procedure described in Example 1, including purification, gives the products of Formula I listed in Table II wherein $R^2=R^4=H$; $R=R^3=OH$.

EXAMPLE 8

Alternate Route to Products in Table II and Related Diacids

Treatment of 3-amino-1-t-butoxycarbonyl- methylperhydroazonin-2-one with 4N HCl in ethyl acetate affords 3-amino-1-carboxymethylperhydroazonin-2-one hydrochloride. A solution of 100 mg of this amine hydrochloride and 3-5 equivalents of an ester listed in Table I is prepared in 6 ml ethanol. A solution of 1.5-3 equivalents of sodium cyanoborohydride in 1.5 ml ethanol is added over a period of 6-24 hours. The reaction mixture is then diluted with water and made acidic to destroy excess sodium cyanoborohydride, then washed with ether. The aqueous solution is passed over a column of acid ion exchange resin, eluting first with water. The column is next eluted with 5% pyridine in water to afford the products of Formula I listed in Table II.

Saponifiation of these esters yields the products described in Example 7.

EXAMPLE 9

Alternate Route to Diacid Products

A solution of 100 mg of 3-amino-1-carboxymethylperhydroazonin-2-one hydrochloride in water is adjusted to pH 7 with dilute, caustic and then freeze dried. The resulting product and 3-5 equivalents of an o-ketoacid listed in Table III below are dissolved in 6 ml ethanol and 1 gm of 3A powdered molecular seives is added. A soluton of 1.5-3 equivalents of sodium cyanoborohydride in 1.5 ml ethanol is added over a period of 6-24 hours. The reaction is then made acidic to destroy excess reducing agent. The solution is then passed over a column of acidic ion exchange resin, eluting first with water. The product is eluted with 5% pyridine solution to afford the diacids of Formula I described in Example 7.

EXAMPLE 10

Ester products derived from 3-amino-1-(1-carboxyethyl)perhydroazonin-2-one

3-Amino-1-(1-carboxyethyl)perhydroazonin-2-one (Isomer A), described in Example 2, is reacted with the ketoesters listed in Table I in the presence of sodium cyanoborohydride as described in Example 8. The products of Formula I which are obtained are listed in Table II wherein $R^3=OH$ and $R^2=CH_3$ and $R^4=H$.

EXAMPLE 11

Diester products derived from 3-amino-1-(1-carboxyethyl)perhydroazonin-2-one

3-Amino-1-(1-ethoxycarbonylethyl)perhydroazonin-2-one (Example 16) is reductively condensed with the ketoesters listed in Table I to afford the diester products listed in Table II wherein $R^2=CH_3$ and $R^3=C_2H_5O$ and $R^4=H$.

p EXAMPLE 12

Diacid Products derived from 3-amino-1-(1-carboxyethyl)perhydroazonin-2-one

3-Amino-1-(1-carboxyethyl)perhydroazonin-2-one is reductively condensed with the α-ketoacids listed in Table III below following the procedure of Example 9. The products of Formula I which are obtained are listed in Table II wherein: $R^2=CH_3$, $R^4=H$, and $R=R^3=OH$ are isolated.

TABLE III

| | α-Ketoacids |
|---|---|
| x | 2-oxo-4-phenylbutyric acid |
| y | 4-p-chlorophenyl-2-oxobutyric acid |
| z | 4-(3-indolyl)-2-oxobutyric acid |
| aa | 2-oxo-4-(2-thienyl)butyric acid |
| bb | 2-oxo-4-(2-naphthyl)butyric acid |
| cc | 4-p-hydroxyphenyl-2-oxobutyric acid |
| dd | phenoxypyruvic acid |
| ee | 2-oxo-5-phenylpentanoic acid |
| ff | 4-p-methoxyphenyl-2-oxobutyric acid |
| gg | 5-methyl-2-oxohexanoic acid |
| hh | 2-oxo-6-phthalimidohexanoic acid |

EXAMPLE 13

Alternate Routes to Diacid Products Derived From 3-amino-1-(1-carboxyethyl)perhydroazonin-2-one Saponification of the esters described in Examples 10 and 11 with dilute base as described in Example 5 followed by purification of the products by ion exchange as described in Example 1 affords the diacids of Formula I listed in Table II wherein $R^2=CH_3$, $R=R^3=OH$, and $R^4=H$.

Alternatively, benzyl esters may be removed by catalytic hydrogenation over 10% palladium on charcoal. Filtration and concentration of the reaction mixture yields the products of Formula I described above.

EXAMPLE 14

Mono- and Mixed Diesters of Formula I ($R^2=R^4=H$)

Using the same procedures as in Examples 3 and 6 but substituting some of the α-ketoacids and α-ketoesters from Tables I and III and the esters from Example 15, one obtains the products listed in Table IV below.

TABLE IV

| Monoesters and Mixed Diesters of Formula I ($R^2 = R^4 = H$) | | | |
|---|---|---|---|
| | R | $R^1$ | $R^3$ |
| ii | ethoxy | phenethyl | benzyloxy |
| jj | hydroxy | p-chlorophenethyl | benzyloxy |
| kk | hydroxy | 2-napthylethyl | benzyloxy |
| ll | hydroxy | 3-methylbutyl | benzyloxy |
| mm | hydroxy | 4-aminobutyl | benzyloxy |
| nn | hydroxy | phenethyl | ethoxy |
| oo | benzyloxy | phenethyl | ethoxy |
| pp | hydroxy | phenethyl | benzyloxy |

EXAMPLE 15

Esters of 3-amino-1-carboxymethylperhydroazonin-2-one

Reaction of 3-amino-1-t-butylcarbonylmethyl-perhydroazonin-2-one (Example 1) with thionyl chloride-ethanol or thionyl chloride-benzyl alcohol followed by concentration and liberation of the free amino ester affords 3-amino-1-ethoxycarbonylmethylperhydroazonin-2-one and 3-amino-1-benzyloxycarbonylmethylperhydroazonin-2-one, respectively.

EXAMPLE 16

Esters of 3-amino-1-(1-carboxyethyl)perhydroazonin-2-one

Reaction of 3-amino-1-(1-carboxyethyl)- perhydroazonin-2-one (Isomer A, Example 2) with thionyl chloride-ethanol or thionyl chloride-benzyl alcohol followed by concentration and liberation of the free amino ester affords 3-amino-1-(1-ethoxycarbonylethyl)-perhydroazonin-2-one and 3-amino-1-(1-benzyloxycarbonylethyl)perhydroazonin-2-one, respectively.

EXAMPLE 17

1-Ethoxycarbonylmethyl-3-(1-ethoxycarbonyl-3-phenylpropyl)aminoperhydroazonin-2-one 1-t-Butoxycarbonylmethyl-3-(1-ethoxycarbonyl-3-phenylpropyl)aminoperhydroazonin-2-one (Example 1) is treated with hydrogen chloride in ethanol followed by concentration and partitioning of the residue between aqueous potassium carbonate and ethyl acetate. Drying and concentration of the organic phase affords the title product.

EXAMPLE 18

Mono- and Mixed Diesters of Formula I ($R^2=CH_3$, $R^4=H$)

Using the same procedure as in Examples 3 and 6 but substituting some of the β-ketoacids and α-ketoesters from Tables I and III and the esters from Example 16, one obtains the products listed in Table IV wherein $R^2=CH_3$.

EXAMPLE 19

1-Carboxymethyl-3-[(1-carboxy-9-methyl-3-phenylpropyl)amino]perhydroazonin-2-one and monoethyl ester Hydrogenate a sample of 1,3,4,7,8,9-hexahydro-9-methyl-2H-azonin-2-one [Wilson, *J. Org. Chem.* 44, 330 (1979)] in ethanol over Pd/C catylyst to obtain 9-methylperhydroazonin-2-one. Treat with PBr5 as described by Nagasawa [*J. Med. Chem.* 14, 501 (1971)] to obtain 3-bromo-9-methyl-perhydroazonin-2-one. Following the method of Example 1, convert this to the various isomers of 1-carboxymethyl-3-[(1-ethoxycarbonyl-3-phenylpropyl)amino]-9-methylperhydroazonin-2-one (I, $R=OC_2H_5$, $R_1=CH_2CH_2\phi$, $R_2=H$, $R_3=OH$, $R_4=CH_3$).

Hydrolze the monoesters with NaOH as described in Example 1 to obtain the corresponding diacids.

EXAMPLE 20

1-Carboxymethyl-3-[(1-carboxy-9-n-butyl-3-phenylpropyl) amino]perhydroazonin-2-one and monoethyl ester Starting with 1,3,4,7,8,9-hexahydro-9-n-butyl-2H-azonin-2-one [Wilson, quoted above], hydrogenate the double bond and continue by the method of Example 19 to obtain 1-carboxymethyl-3-[(1-ethoxycarbonyl-3-phenylpropyl)-amino]-9-n-butylperhydroazonin-2-one (I, $R=OEt$, $R_1=C_2H_5\phi$, $R_2=H$, $R_3=OH$, $R_4=n-C_4H_9$). Hydrolyze with NaOH as in Example 1 to obtain the corresponding diacid.

EXAMPLE 21

Compressed Tablet containing 50 mg of active ingredient

| | Per tablet, Mg. |
|---|---|
| 1-Carboxymethyl-3-(1-carboxy-3-phenyl-1-propyl)aminoperhydro-azonin-2-one | 50 |
| Calcium phosphate dibasic | 200 |
| Ethyl cellulose (as 5% solution in ethanol) | 5 |
| Unmixed granulation | 255 |
| Add: | |
| Starch, corn | 14 |
| Magnesium stearate | 1 |
| | 270 |

Directions: Mix the active ingredient above and calcium phosphate and reduce to a No. 60 mesh powder. Granulate with Ethocel in alcohol and pass the wet granulation through a No. 10 screen. Dry the granulation at 110° F. for 12–18 hrs. Dry grind to a No. 20 mesh. Incorporate the "adds" and compress into tablets each weighing 270 mg.

EXAMPLE 22

Dry filled capsule containing 50 mg of active ingredient.

| | Per capsule, mg |
|---|---|
| 1-(1-Carboxy-1-ethyl)-3-[(1-carboxy-3-phenyl-1-propyl)amino]perhydroazonin-2-one | 50 |
| Lactose | 273 |
| Magnesium stearate | 2 |
| Mixed Powders | 325 |

Mix the active ingredient above, lactose, and magnesium stearate and reduce to a No. 60 mesh powder. Encapsulate, filling 325 mg in each No. 2 capsule.

The above formulations can be employed to prepare compressed tablets or capsules of other novel compounds of this invention hereinbefore described.

The above examples describe the preparation of certain compounds which are illustrative of the novel compounds of this invention, and certain specific dosage forms suitable for administering the novel compounds. It is to be understood, however, that the invention is not to be limited to the specific compounds described in the examples or by the specific reaction conditions described for the preparation of these compounds or by the specific ingredients included in the pharmaceutical preparations, but is to be understood to embrace variations and modifications thereof.

What is claimed is:

1. A compound of the formula:

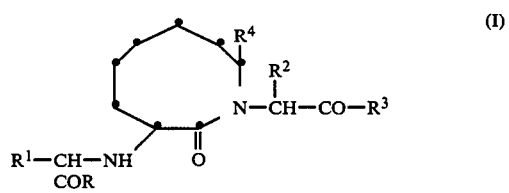

wherein
R and $R^3$ are the same or different and are
hydroxy,
lower alkoxy,
lower alkenoxy,
aryloxy,
arloweralkoxy;
$R^1$ is
hydrogen,
alkyl, alkenyl and alkynyl of up to 12 carbon atoms which include branched groups, cycloalkyl of unsubstituted $C_3-C_{10}$; substituted loweralkyl wherein the substituent(s) can be halo, lower alkoxy, hydroxy, aryloxy, amino, loweralkylamino, aminoloweralkylthio, aminoloweralkoxy, diloweralkylamino, acylamino, arylamino, guanidino, phthalimido, mercapto, loweralkylthio, arylthio, carboxy, carboxamido or carboloweralkoxy, arloweralkyl, arloweralkenyl, heteroarlower alkyl or heteroarlower alkenyl, substituted arloweralkyl, or substituted heteroarlower alkyl, wherein the aryl or heteroaryl substituents are halo, dihalo, lower alkyl, hydroxy, lower alkoxy, amino, aminomethyl, phenyloxy, acylamino, diloweralkylamino, loweralkylamino, carboxyl, haloloweralkyl, or aroyl;
arloweralkyl or heteroarloweralkyl substituted on the alkyl portion by amino, hydroxy or acylamino;
$R^2$ and $R^4$ are hydrogen or lower alkyl;
and, the pharmaceutically acceptable salts thereof wherein in said R—$R^4$ groups, unless otherwise indicated, aryl and the prefix "ar" denote unsubstituted aromatic ring or rings of $C_6-C_{12}$, acyl denotes an organic radical derived from carboxylic acid, and heteroaryl denotes an aryl group containing an N, O or S heteroatom.

2. A compound of the formula:

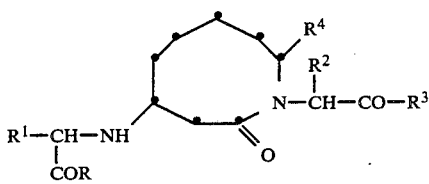

wherein

R and R³ are independently hydroxy, lower alkoxy, or benzyloxy;

R² and R⁴ are hydrogen or lower alkyl;

R¹ is alkyl having from 1 to 8 carbon atoms, substituted lower alkyl wherein the alkyl group has 1-5 carbon atoms and the substituent is amino, acylamino, hydroxy, aminoloweralkylthio, aminoloweralkoxy, arylthio, aryloxy or arylamino, aralkyl or heteroaralkyl wherein the alkyl portion has 1 to 3 carbon atoms or substituted arloweralkyl and substituted heteroarloweralkyl wherein the alkyl groups have 1 to 3 carbons optionally substituted with amino, hydroxy, or acylamino and wherein the substituents on the aryl or heteroaryl group are halo, dihalo, amino, aminoalkyl, hydroxy, lower alkoxy or lower alkyl, phenoxy or benzoyl;

and, the pharmaceutically acceptable salts thereof wherein in said R—R⁴ groups, unless otherwise indicated, aryl and the prefix "ar" denote unsubstituted aromatic ring or rings of $C_6$-$C_{12}$, acyl denotes an organic radical derived from carboxylic acid, and heteroaryl denotes an aryl group containing an N, O or S heteroatom.

3. A compound of the formula:

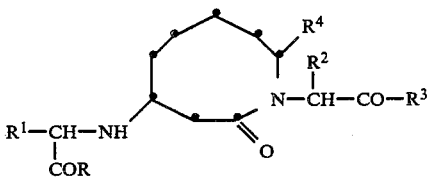

wherein

R¹ is alkyl from 1 to 8 carbon atoms, phenyl lower alkyl, indolyl lower alkyl, halophenyl lower alkyl, phenoxy lower alkyl, amino lower alkyl, phenyl thio lower alkyl, aminoethylthioloweralkyl, aminoethyloxyloweralkyl;

R² is hydrogen, or lower alkyl;

R⁴ is hydrogen

R and R³ are independently hydroxy, lower alkoxy, or benzyloxy;

and, the pharmaceutically acceptable salts thereof.

4. A compound of the formula

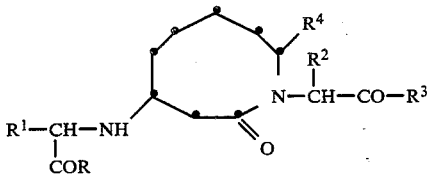

wherein

R¹ is phenyl lower alkyl, indolyl lower alkyl, halo phenyl lower alkyl or amino lower alkyl;

R² and R⁴ are hydrogen;

R and R³ are independently hydroxy, lower alkoxy, or benzyloxy;

and, the pharmaceutically acceptable salts thereof.

5. A compound of claim 4 which is 1-carboxymethyl-3-[(1-carboxy-3-phenylpropyl)amino]perhydroazonin-2-one.

6. A compound of Claim 4 which is 1-carboxymethyl-3-[(1-ethoxycarbonyl-3-phenylpropyl)amino]perhydroazonin-2-one.

7. A pharmaceutical composition useful in the treatment of hypertension which comprises a pharmaceutically acceptable carrier and an antihypertensively effective amount of an amino acid compound of the formula:

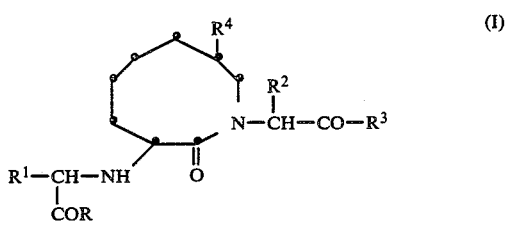

wherein

R and R³ are the same or different and are
hydroxy,
lower alkoxy,
lower alkenoxy,
aryloxy,
arloweralkoxy, R¹ is
hydrogen,
alkyl, alkenyl and alkynyl of up to 12 carbon atoms which include branched groups,
cycloalkyl of unsubstituted $C_3$-$C_{10}$;
substituted loweralkyl wherein the substituent can be halo, lower alkoxy, hydroxy, aryloxy, amino, loweralkylamino, aminoloweralkylthio, aminoloweralkoxy, diloweralkylamino, acylamino, arylamino, guanidino, phthalimido, mercapto, loweralkylthio, arylthio, carboxy, carboxamido or carboloweralkoxy,
arloweralkyl, arloweralkenyl, heteroarlower alkyl or heteroarlower alkenyl,
substituted arloweralkyl or substituted heteroarlower alkenyl, wherein the aryl or heteroaryl substituents are halo, dihalo, lower alkyl, lower alkoxy, amino, aminomethyl, phenyloxy, acylamino, diloweralkylamino, loweralkylamino, carboxyl, haloloweralkyl, or aroyl;
arloweralkyl or heteroarloweralkyl substituted on the alkyl portion by amino or acylamino;

R² and R⁴ are hydrogen or lower alkyl; and, the pharmaceutically acceptable salts thereof wherein in said R—R⁴ groups, unless otherwise indicated, aryl and the prefix "ar" denote unsubstituted aromatic ring or rings of $C_6$-$C_{12}$, acyl denotes an organic radical derived from carboxylic acid, and heteroaryl denotes an aryl group containing an N, O or S heteroatom.

8. A pharmaceutical composition useful in the treatment of hypertension which comprises a pharmaceutically acceptable carrier and an antihypertensivity effective amount of an amino acid compound of the formula:

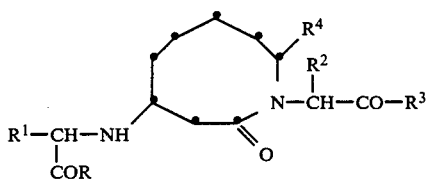

(I)

wherein
R¹ is phenyl lower alkyl, indolyl lower alkyl, halo phenyl lower alkyl or amino lower alkyl;
R² and R⁴ are hydrogen;
R and R³ are independently hydroxy, lower alkoxy or benzyloxy;
and, the pharmaceutically acceptable salts thereof.

9. A process for preparing compounds of the formula:

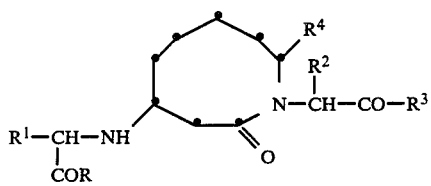

(I)

wherein
R and R³ are the same or different and are
  hydroxy,
  lower alkoxy,
  lower akenoxy,
  aryloxy,
  arloweralkoxy;
R¹ is
  hydrogen,
  alkyl, alkenyl and alkynyl of up to 12 carbon atoms which include branched groups, cycloalkyl of unsubstituted $C_3$-$C_{10}$;
  substituted loweralkyl wherein the substituent can be halo, lower alkoxy, hydroxy, aryloxy, amino, loweralkylamino, aminoloweralkylthio, aminoloweralkoxy, diloweralkylamino, acylamino, arylamino, guanidino, phthalimido, mercapto, loweralkylthio, arylthio, carboxy, carboxamido or carboloweralkoxy,
  arloweralkyl, arloweralkenyl, heteroarlower alkyl or heteroarlower alkenyl,
  substituted arloweralkyl, or substituted heteroarlower alkyl, or substituted heteroarlower alkenyl, wherein the substituents are halo, dihalo, lower alkyl, lower alkoxy, amino, aminomethyl, phenyloxy, acylamino, diloweralkylamino, loweralkylamino, carboxyl, haloloweralkyl, or aroyl;
  arloweralkyl or heteroarloweralkyl substituted on the alkyl portion by amino, hydroxyl, or acylamino; and,
R² and R⁴ are hydrogen or lower alkyl;
wherein in said R—R⁴ groups, unless otherwise indicated, aryl and the prefix "ar" denote unsubstituted aromatic ring or rings of $C_6$-$C_{12}$, acyl denotes an organic radical derived from carboxylic acid, and heteroaryl denotes an aryl group containing an N, O or S heteroatom; which comprises reductively alkylating a compound of the formula:

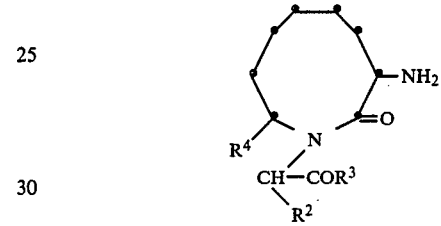

with a compound of the formula:

wherein R and R¹ are as defined above followed by removal of protecting groups, if necessary, to yield the desired product and, if desired, isolating the biologically more active isomer by chromatography, fractional crystallization, or resolution with an appropriate optically active acid or base and, if desired, preparing a salt of the desired product by conventional means.

* * * * *